(12) United States Patent
Blancke (10) Patent No.: US 11,724,039 B2
(45) Date of Patent: Aug. 15, 2023

(54) INJECTION DEVICE

(71) Applicant: SANOFI, Paris (FR)

(72) Inventor: Stefan Blancke, Frankfurt am Main (DE)

(73) Assignee: Sanofi, Paris (FR)

(*) Notice: Subject to any disclaimer, the term of this patent is extended or adjusted under 35 U.S.C. 154(b) by 519 days.

(21) Appl. No.: 16/976,202

(22) PCT Filed: Mar. 25, 2019

(86) PCT No.: PCT/EP2019/057392
§ 371 (c)(1),
(2) Date: Aug. 27, 2020

(87) PCT Pub. No.: WO2019/185517
PCT Pub. Date: Oct. 3, 2019

(65) Prior Publication Data
US 2021/0038821 A1 Feb. 11, 2021

(30) Foreign Application Priority Data
Mar. 28, 2018 (EP) .................... 18305345

(51) Int. Cl.
*A61M 5/315* (2006.01)
*A61M 5/24* (2006.01)
*A61M 5/31* (2006.01)

(52) U.S. Cl.
CPC .......... *A61M 5/3155* (2013.01); *A61M 5/24* (2013.01); *A61M 5/31583* (2013.01);
(Continued)

(58) Field of Classification Search
CPC .. A61M 5/3155; A61M 5/24; A61M 5/31583; A61M 2005/3126;
(Continued)

(56) References Cited

U.S. PATENT DOCUMENTS

2016/0074588 A1 3/2016 Butler et al.
2017/0128670 A1 5/2017 Marsh et al.
(Continued)

FOREIGN PATENT DOCUMENTS

CN 102202711 9/2011
CN 107029320 8/2017
(Continued)

OTHER PUBLICATIONS

PCT International Search Report and Written Opinion in International Appln. No. PCT/EP2019/057392, dated Aug. 2, 2019, 9 pages.
(Continued)

*Primary Examiner* — Dung T Ulsh
(74) *Attorney, Agent, or Firm* — Fish & Richardson P.C.

(57) ABSTRACT

An injection device comprises a housing with a receptacle for a product, a dosing mechanism for setting a product dosage to be administered and for displaying the product dosage that has been set, and a dispensing mechanism for dispensing the product. The dosing mechanism comprises a dosing sleeve which is rotatable relative to the housing in a first direction for setting a product dosage and which is rotatable relative to the housing in a second, opposite direction for correcting or dispensing a product dosage. The dispensing mechanism comprises a piston rod, at least one sleeve, and a clutch. The device further comprises a first detector for detecting movement of the clutch relative to the dosing sleeve and/or the housing and/or the at least one sleeve and a data processing unit connected to the first detector for reading, storing, processing, transmitting, and/or displaying signals received from the first detector.

19 Claims, 2 Drawing Sheets

(52) U.S. Cl.
CPC .............. *A61M 2005/3126* (2013.01); *A61M 2205/0227* (2013.01); *A61M 2205/0233* (2013.01); *A61M 2205/3317* (2013.01); *A61M 2205/50* (2013.01)

(58) Field of Classification Search
CPC .. A61M 2205/0227; A61M 2205/0233; A61M 2205/3317; A61M 2205/50
See application file for complete search history.

(56) References Cited

U.S. PATENT DOCUMENTS

| | | | | |
|---|---|---|---|---|
| 2018/0036484 | A1* | 2/2018 | Andersen | G16H 20/10 |
| 2018/0126088 | A1* | 5/2018 | Radmer | A61M 5/3158 |
| 2019/0192782 | A1* | 6/2019 | Pedersen | A61M 5/3157 |

FOREIGN PATENT DOCUMENTS

| | | | |
|---|---|---|---|
| CN | 107405449 | 11/2017 | |
| EP | 2814547 | 12/2014 | |
| EP | 3067081 | 9/2016 | |
| EP | 3067081 A1 * | 9/2016 | ............. A61M 5/20 |
| JP | 2012-507314 | 3/2012 | |
| JP | 2017-534356 | 11/2017 | |
| WO | WO 2010/052275 | 5/2010 | |
| WO | WO 2013/170392 | 11/2013 | |
| WO | WO 2014/117944 | 8/2014 | |
| WO | WO 2014/161954 | 10/2014 | |
| WO | WO 2016/001304 | 1/2016 | |
| WO | WO 2016/016184 | 2/2016 | |
| WO | WO 2016/050902 | 4/2016 | |
| WO | WO 2016/120428 | 8/2016 | |
| WO | WO 2016/142511 | 9/2016 | |
| WO | WO 2017/134131 | 8/2017 | |

OTHER PUBLICATIONS

PCT International Preliminary Report on Patentability in International Application No. PCT/EP2019/057392, dated Sep. 29, 2020, 7 pages.

* cited by examiner

INJECTION DEVICE

CROSS REFERENCE TO RELATED APPLICATIONS

The present application is the national stage entry of International Patent Application No. PCT/EP2019/057392, filed on Mar. 25, 2019, and claims priority to Application No. EP 18305345.3, filed on Mar. 28, 2018, the disclosures of which are incorporated herein by reference.

TECHNICAL FIELD

The present disclosure is generally directed to an injection device, i.e. a drug delivery device for selecting and dispensing a number of user-variable doses of a medicament.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user-variable doses of a medicament. The present disclosure is not directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is applicable for both types of devices, i.e. for disposable devices as well as for reusable devices.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

An injection device comprising a housing with a receptacle for the product, a dosing mechanism for setting a product dosage to be administered and for displaying the set product dosage and a dispensing mechanism for dispensing the product is known e.g. from EP 2 814 547 B1 which discloses a manually driven device or from WO 2014/117944 A1, WO 2016/016184 A1 or WO 2017/134131 A1 which disclose spring driven devices.

These known devices are provided with a display providing a visual feedback to a user regarding the actually set dose size. The display of such devices typically involves a number sleeve with a series of numbers corresponding to dose sizes being provided on the outer surface of the number sleeve such that only the actually set dose is visible through an opening or window in the housing. Especially for visually impaired users, it may be desirable to get such information in a different manner, for example on a separate display unit and/or such that the information may be stored.

SUMMARY

It is an object of the present disclosure to provide an improved alternative to the above solutions. Especially, it is an object of the present disclosure to provide an injection device or a drug delivery device providing information to users regarding the set dose size.

This object is solved by an injection device according to claim 1.

An injection device according to the present disclosure comprises a housing with a receptacle for the product, a dosing mechanism for setting a product dosage to be administered and for displaying the set product dosage and a dispensing mechanism for dispensing the product. The dosing mechanism may comprise a dosing sleeve, e.g. a number sleeve with numbers or symbols provided on its outer surface, which is rotatable relative to the housing in a first direction for setting a product dosage and which is rotatable relative to the housing in a second, opposite direction for correcting or dispensing a product dosage. The dispensing mechanism of the device may comprise a piston rod, which is moveable relative to the housing in a dispensing direction in order to eject the set product dosage in a dispensing stroke corresponding to the set product dosage, at least one sleeve, which is rotatable together with the dosing sleeve relative to the housing in the second direction in order to eject the set product dosage, and a clutch interposed between the dosing sleeve and the at least one sleeve and rotatable with the dosing sleeve and/or the at least one sleeve. The present disclosure is based on the idea that detecting movements of one or more component parts of the injection device may be used to identify e.g. the actually set dose size and/or the actual operation mode of the device. If a relative rotation between the clutch and further component parts of the device occurs, e.g. in increments corresponding to dose units, this relative rotation may be used to identify the actually set dose size. For example, the device may further comprise at least a first detector for detecting movement of the clutch relative to the dosing sleeve and/or the housing and/or the at least one sleeve and a data processing unit connected to the first detector for reading, storing, processing, transmitting and/or displaying signals received from the first detector.

In an exemplary embodiment, the clutch may comprise first ratchet teeth for engaging corresponding first teeth of the dosing sleeve such that relative incremental rotation of the dosing sleeve with respect to the clutch in one direction, preferably the first direction, is permitted while prevented in the opposite direction and second ratchet teeth for engaging corresponding second teeth of the at least one sleeve such that relative incremental rotation of the clutch with respect to the at least one sleeve in one direction, preferably the second direction, is permitted while prevented in the opposite direction. For example, the teeth may have the form of saw-teeth. The clutch may have the form of a toothed ring, like the toothed ring provided interposed between the dosing sleeve and the coupling sleeve in EP 2 814 547 B1. Preferably, the first ratchet teeth and the second ratchet teeth are located on the clutch facing in opposite axial directions. The incremental or stepwise rotation may cause a clicking sound every time a pair of teeth re-engages thereby providing an acoustical and/or tactile feedback to the user. Typically, one click corresponds to one dose unit such that counting the number of clicks enables a user to identify the set dose size.

The present disclosure is suitable for devices permitting dose setting and dispensing the set dose as well as devices permitting dose setting, dose correcting and dispensing the set dose. In this respect dose correcting is defined as reducing the size of a set dose without dispensing the set dose. In other words, the term dose setting is used indicating increasing the set dose, while the term dose correcting is used indicating decreasing the set dose. Dose setting and dose correcting may include relative movement of the first and/or second ratchet teeth. Thus, detecting the clicks produced during dose setting and during dose correcting may be used to identify the resulting dose size.

The first detector and the data processing unit are preferably adapted to detect at least one of a rotational movement of the clutch, an angle of rotation the rotational movement of the stop wheel and a direction of the rotational movement of the stop wheel. Detecting start and stop of the rotational movement is indicative of the device being used or not. Further, the angle of rotation is indicative of the size of a dose which is selected and/or dispensed by the drug delivery device. The direction of the rotational movement is indicative of the operation mode of the device, for example if the clutch rotates in a first direction during dose setting and rotates in a second, opposite direction during dose correction and/or dose dispensing. Summarizing, detecting the movement of the clutch provides the required information for giving a feedback to the user regarding the operation mode of the device. Further, the data processing unit may be adapted to provide information about the dose size and/or amount of product ejected from the device by the dispensing mechanism and/or the maximum dose set by the dosing mechanism based on a rotation protocol containing data received from the first detector. Either the first detector and/or a further detector are adapted to detect the relative incremental rotation between the clutch and any further component part of the device, e.g. the dosing sleeve and/or the housing and/or the at least one sleeve, in the first direction and/or in the second direction.

As mentioned above, the relative incremental rotation between the clutch and the dosing sleeve and/or the at least one sleeve may generate an acoustic feedback to a user.

Optionally, the first detector comprises at least one sensor for detecting this acoustic feedback generated by relative incremental rotation between the clutch and the dosing sleeve and/or the at least one sleeve. The sound generated during dose setting may differ from the sound generated during dose correcting such that the sensor may differentiate between dose setting and dose correcting. Other features may be used in conjunction or as an alternative to identify whether a dose is set or corrected, e.g. detecting the direction of rotation of the clutch and/or other component parts.

As an alternative or in addition to detecting an acoustical feedback, the first ratchet teeth and/or the second ratchet teeth may be coated with a galvanic conductive material and at least one of the first teeth and/or at least one of the second teeth are provided with an elastic galvanic contact arranged for engaging with the galvanic conductive material at each rotational increment. In other words, the first detector comprises the elastic galvanic contact and the galvanic conductive material and each incremental rotational movement provides an electric signal which may be counted by the data processing unit. The resulting dose is e.g. calculated in counting the signals at the dialing end, e.g. the interface between the dose sleeve and the clutch, and subtracting the counted signals of the correcting end, e.g. the interface between the clutch and the at least one sleeve.

According to a further embodiment, the first detector comprises at least one mechanical switch which is provided between the first ratchet teeth and the first teeth and/or between the second ratchet teeth and the second teeth and is arranged for detecting engaging of the teeth at each rotational increment. Each switch engages with the respective ratchet teeth at each incremental rotation and thus produces an electrical signal. The dose calculation is done in a similar manner by the data processing unit as mentioned above.

In a further embodiment, the first detector comprises at least one of a magnetic sensor and an inductive sensor, e.g. suitable to detect the rotational position of the dosing sleeve and/or the clutch. Data received from such a sensor may be analyzed by an add-on device attached e.g. to a button or to the dosing sleeve. This method may be used to calculate the set dose size taking into account a possible dose correction. In other words, it is possible to detect the chosen dose by analyzing the rotational positions of the dosing sleeve and the clutch.

The injection device may further comprise a second detector for detecting the relative axial position of the clutch and the dosing sleeve. The data processing unit may be connected to the second detector for reading, storing, processing, transmitting and/or displaying signals received from the second detector. The additional detector may be required to differentiate between dose setting, dose correcting and/or dose dispensing be determining the relative axial position of the dosing sleeve relative to the clutch. For example, the second detector comprises at least one of a magnetic sensor and an inductive sensor.

Using a magnetic sensor or an inductive sensor may require that the clutch and/or the dosing sleeve comprise a metallic material. For example, the dosing sleeve and/or the clutch may be metallized, coated, printed or additives may be added to the component parts, which typically mainly comprise a plastic material.

The data processing unit may be adapted to provide information about the device being in its dose setting mode, its dose correction mode or its dose dispensing mode based on data received from the first detector and the second detector. The data processing unit may be provided within the housing of the injection device. For example, the data processing unit and the first and second detector may be permanently provided within the housing of the injection device. This includes embodiments in which the data processing unit is connected to at least one of the first and second detector by wire. As an alternative, the data processing unit may be detachable from the housing and/or may be connected to at least one of the first and second detector by means of a wireless connection. In other words, the data processing unit may be an add-on device which may be attached to the housing and removed from the housing. Examples for wireless communication between the data processing unit and at least one detector may include communication via a near field communication (NFC) or via Bluetooth (BT).

Further, the data processing unit may be adapted to send data to and/or receive data from a separate data processing and/or display device, e.g. portable handheld electronic devices, via a near field communication (NFC) or via Bluetooth (BT). The data may be queried after each use (injection) and read out or an add-on device could read, process and store the data and send a rotation protocol via to another device for further processing. The add-on device may alternatively transmit unprocessed data.

The at least one sleeve may be a component part which is in direct engagement with the piston rod. For example, the at least one sleeve may be a drive sleeve which is splined to the piston rod or which is in threaded engagement with the piston rod. However, as an alternative, the at least one sleeve may be a component part which is indirectly coupled to the piston rod, for example with a clutch or a transmission element interposed between the at least one sleeve and the piston rod. The at least one sleeve may be permanently coupled to the piston rod or may be selectively coupled to the piston rod only in a certain mode of the injection device, for example during dose dispensing. The injection device may comprise two sleeves, which are rotatable relative to the housing in order to eject the set product dosage and which are rotationally constrained relative to each other but displaceable relative to each other in the dispensing direction. The second detector may detect actuation, i.e. rotation, of one of these sleeves or of both sleeves.

The injection device typically comprises a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010), H-(Lys)6-des Pro36 [Asp28] Exendin-4(1-39)-Lys6-NH2, des Asp28 Pro36, Pro37, Pro38Exendin-4(1-39)-NH2, H-(Lys)6-des Pro36, Pro38 [Asp28] Exendin-4(1-39)-NH2, H-Asn-(Glu)5des Pro36, Pro37, Pro38 [Asp28] Exendin-4(1-39)-NH2, des Pro36, Pro37, Pro38 [Asp28] Exendin-4(1-39)-(Lys)6-NH2, H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF FIGURES

Non-limiting, exemplary embodiments of the disclosure will now be described with reference to the accompanying drawings, in which.

DETAILED DESCRIPTION

Figure 1:
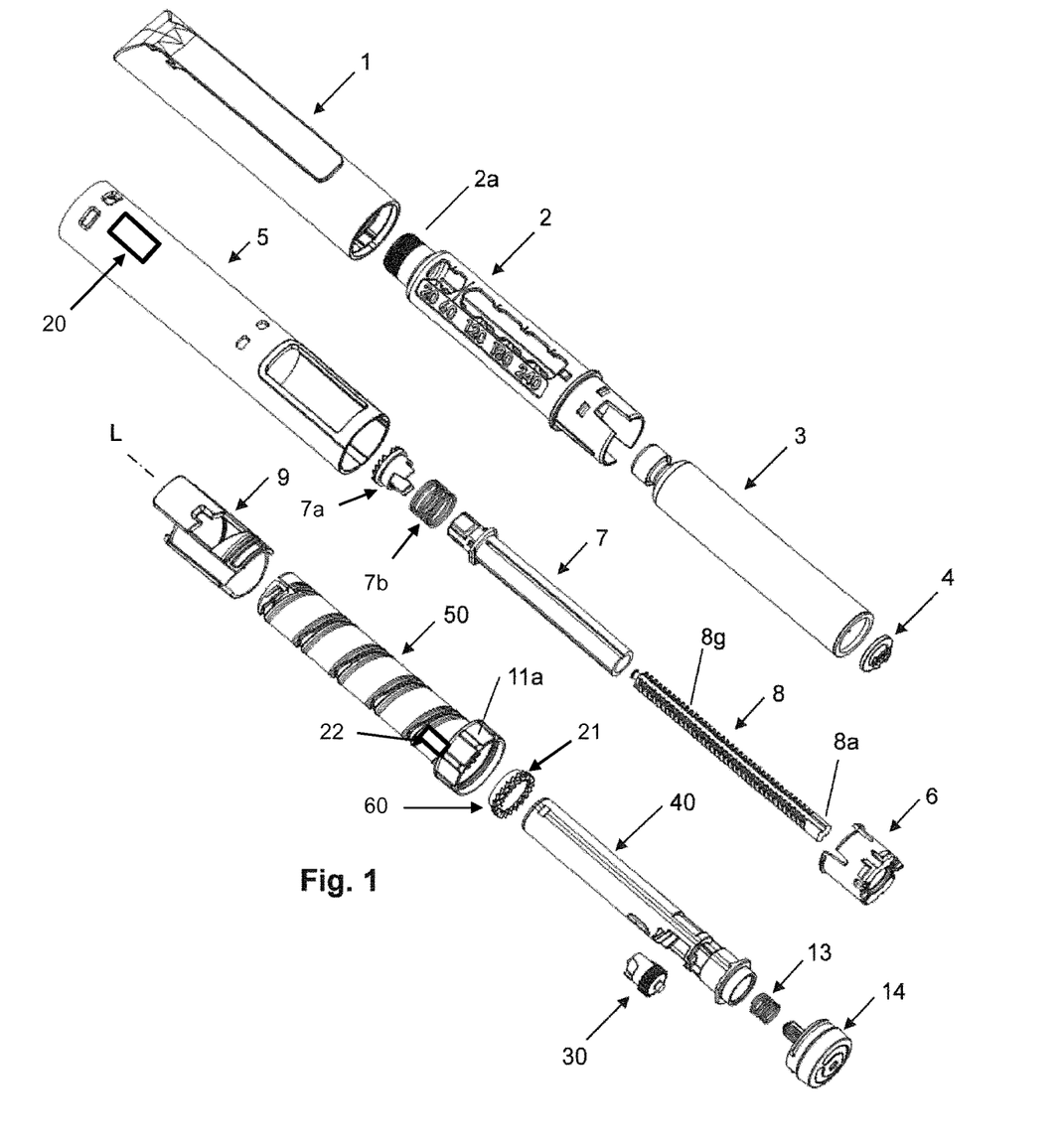
FIG. 1 shows an exploded view of the individual parts of an embodiment of an injection device according to the disclosure.
Figure 2:
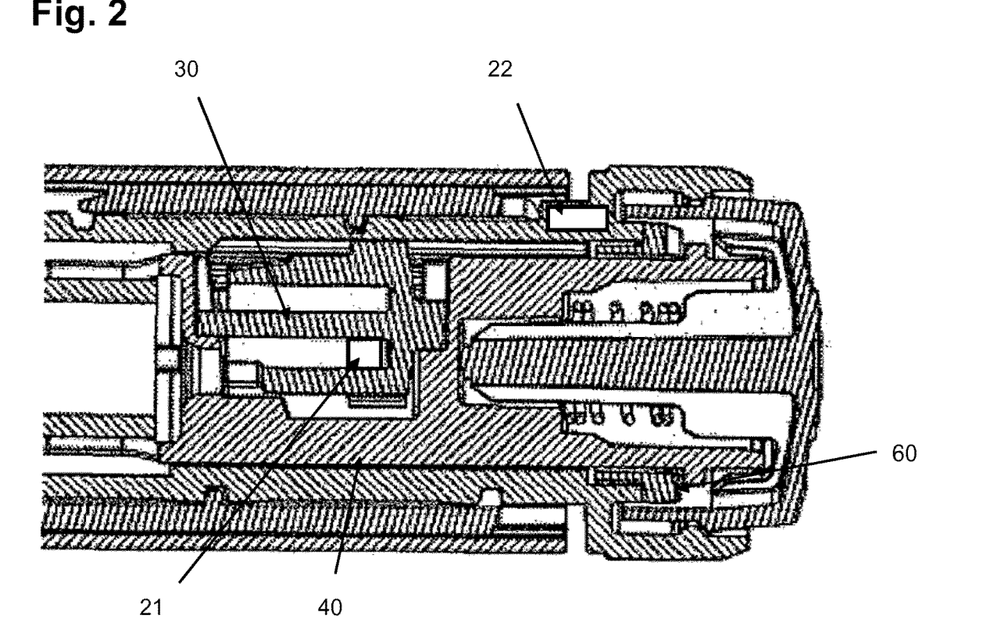
FIG. 2 shows a sectional view of a detail of the embodiment of FIG. 1.
Figure 3A:
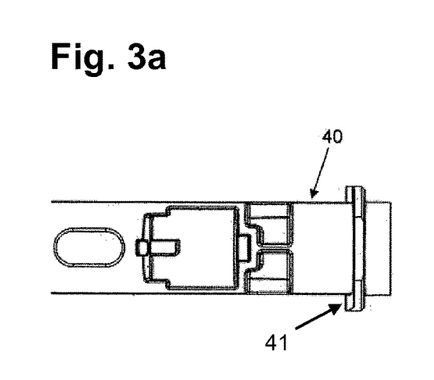
FIGS. 3a-3c show component parts of the injection device of FIG. 1.
Figure 3B:
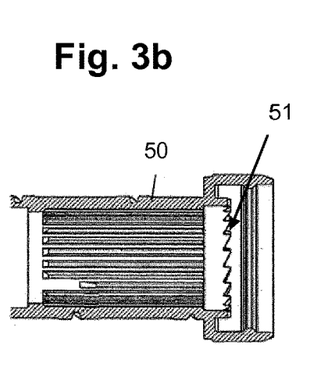
Figure 3C:
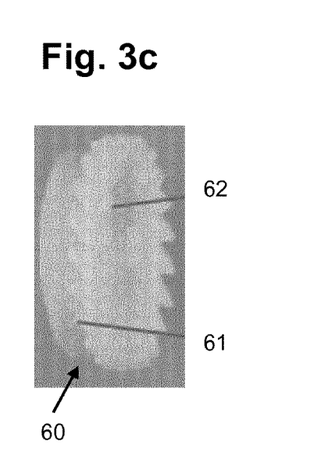

FIG. 1 shows an exploded view of the individual parts of an embodiment of an injection device according to the disclosure. This embodiment is designed as a so-called single-use pen. That is to say, the injection device is issued to the user fully assembled, i.e., with product to be administered.

The typical course of the injection process may be as follows: the user removes the protective cap 1 from the injection device and mounts an injection needle (not shown) on the needle holder 2a of a receptacle 2. Now the dosage can be adjusted via the rotary knob 11a. For this purpose, the rotary knob 11a is turned so that the dosing sleeve 50, which forms a dosing mechanism or is part of a dosing mechanism, is screwed out of the injection device.

The dosing sleeve 50 is screwed out of the injection device until the desired dosage is displayed in the window of the threaded sleeve 9. If an excessively high dosage is inadvertently set, the dosage can be corrected by turning the rotary knob in the opposite direction, whereby the dosing sleeve 50 is screwed back into the housing. The dosing device limits the maximum adjustable dosage to a predetermined value. If there is an attempt to screw the dosing sleeve out of the housing past this value, a radial limit stop on the dosing sleeve 50 and a counter-limit stop on the threaded sleeve 9 prevent further rotation by mutual interaction. During the dosing and correction movements, the dosing sleeve 50 rotates relative to the coupling sleeve 40. The coupling sleeve 40 is held rotationally fixedly in a form fit or friction fit against the housing 5 by a reverse rotation lock, for example by means of a toothed ring 7a rotationally fixed to the threaded nut 7 and biased axially towards a corresponding set of ratchet teeth on an inner surface of the housing 5 by means of a spring 7b. This ratchet between the housing 5 and the threaded nut 7 may form a clicker generating an audible and/or tactile feedback during dose dispensing as the teeth of ring 7a slip over the corresponding teeth of housing 5.

The coupling sleeve 40 is permanently rotationally locked to the axially stationary threaded nut 7 by splines permitting relative axial movement between the coupling sleeve 40 which is axially entrained by the dosing sleeve 50 and the stationary threaded nut 7. The threaded nut 7 may be retained in the housing 5 by means of an insert 6 holding the threaded nut 7 against the bias of spring 7b. A clutch 60 is shown in FIG. 1 as a toothed ring which is interposed between rotary knob 11a and a flange on coupling sleeve 40 such that relative rotation of the dosing sleeve 50 and the coupling sleeve 40 is permitted during dose setting. FIGS. 2, 3a, 3b and 3c show in detail that the clutch is provided with first ratchet teeth 61 on an end facing towards corresponding first teeth 51 of the dosing sleeve 50 and is provided with second ratchet teeth 62 on an opposite end facing towards corresponding second teeth 41 of the coupling sleeve 40.

The ratchet teeth interface 61, 51 between the dosing sleeve 50 and the clutch 60 is designed such that rotation of the dosing sleeve 50 in a first direction, e.g. during dose setting, is permitted relative to the stationary clutch 60 with teeth 51, 61 slipping over each other and re-engaging in rotational increments. Due to the saw-tooth like design of the teeth 51, 61 relative rotation of the dosing sleeve 50 and the clutch 60 in the opposite direction is prevented. The ratchet teeth interface 62, 41 between the coupling sleeve 40 and the clutch 60 is designed such that rotation of the clutch 60 in a second direction, e.g. during dose correcting, is permitted relative to the stationary coupling sleeve 40 with teeth 41, 62 slipping over each other and re-engaging in rotational increments. Due to the saw-tooth like design of the teeth 41, 62 relative rotation of the coupling sleeve 40 and the clutch 60 in the opposite direction is prevented. Spring 13 keeps the ratchet interfaces 51, 61 and 41, 62 in contact but allows axial displacement of the clutch 60 and/or the coupling sleeve 40 against the bias of spring 13 to allow slipping of the interfaces as described above.

In the embodiments depicted in the Figures, multiple teeth 61, 62, 51 and 41 are shown. However, the function of the injection device would be the same if with the clutch 60 having multiple first ratchet teeth 61 at least one tooth 51 would be provided on the dosing sleeve 50 and vice versa. In the same way, multiple second ratchet teeth 62 may interact with at least one tooth 41 and vice versa. While the torque transmitted by an interface having multiple engaging teeth may be increased compared with only a single pair of teeth engaging, providing only one or only few teeth on one of the component parts may have advantages when providing a sensor in or on this component part.

If the desired dosage has been set, the injection needle can be inserted at the intended position on the body of the user. Then the user pushes the ejection button 14 in the distal axial direction against the bias of spring 13 which is interposed between button 14 and coupling sleeve 40. This axial movement blocks a relative rotation between the coupling sleeve 40 and the dosing sleeve 50 by means of the toothed ring of clutch 60, i.e. the coupling sleeve 40 and the dosing sleeve 50 are rotationally constrained via the clutch 60. In case of further pressure in the distal axial direction, the dosing sleeve begins to move back into the housing in a screwing motion. Because of the established rotational lock between the dosing sleeve 50 and the coupling sleeve 40, the coupling sleeve 40 carries out the same movement as the dosing sleeve 50. Because the coupling sleeve 40 is permanently rotationally locked to the axially stationary threaded nut 7, the rotational movement of the dosing sleeve 50 is transmitted to the threaded nut 7. No axial forces are transmitted to the threaded nut 7, because the coupling sleeve 40 is mounted axially movably on the threaded nut 7. Thus, the rotating threaded nut 7 produces an axial movement of the threaded piston rod 8 in the distal direction, wherein the latter is guided axially and locked rotationally in the housing 5 by means of splines 8a and is in threaded engagement with threaded nut 7 by means of an external thread 8g. The flange 4 acts on the plug of the cartridge 3 and pushes it, corresponding to the displacement of the threaded piston rod 8 in the distal direction as well, wherein the previously set dosage can be ejected or administered. At the end of the administration, when the dosing sleeve has been completely screwed back into the housing, radial stops on the dosing sleeve 50 and the threaded sleeve 9 prevent further ejection and overrotation of the dosing device.

The embodiment of FIG. 1 shows an optional limiting device which ensures that the most recently set dosage can be completely ejected or injected. For this purpose, the dosing sleeve 50 has a coaxially applied inner toothing and the coupling sleeve 40 has a lateral cutout in which the stop wheel 30 is inserted. The function of the limiting device is described in EP 2 814 547 B1 in more detail.

The embodiment of FIG. 1 further shows a data processing unit 20 connected to a first detector 21 and a second detector 22 for reading data responsive to signals received from the first and second detectors 21, 22. The data processing unit 20 is depicted as a component part being disposed on the outer surface of the housing 5. It may be permanently attached to the housing 5 or may be an integral part thereof or may be a separate, detachable unit. The data processing unit 20 may comprise a power supply and a PCB suitable for e.g. data processing, data storing and/or display of information.

The first detector 21 is disposed on the clutch 60. In more detail the first detector 21 may comprise a coating on the ratchet teeth 61, 62 of the clutch. For example, the ratchet teeth 61, 62 are coated with a galvanic conductive material and an, e.g. elastically deformable, galvanic contact is arranged on first teeth 51 and/or second teeth 41 to engage with the galvanic conductive material. Thus, every time the teeth 51, 61 or 62, 41 re-engage an electric signal may be generated or transmitted.

Instead of the first detector 21 being provided at least partially on the clutch 60, the first detector 21 may be provided on the dosing sleeve 50. For example, the first detector 21 may be a magnetic rotation encoder (quadrature), a vibrating structure microelectromechanical systems (MEMS) gyroscope or a combination of an MEMS gyroscope and an accelerometer. These small size devices may be easibily integrated into the dosing sleeve 50. Generally, gyroscopes measure rotational motion. MEMS (microelectromechanical system) gyroscopes are small, inexpensive sensors that measure angular velocity. The units of angular velocity are measured in degrees per second (°/s) or revolutions per second (RPS). Hence, when determining the duration of the measurement the rotation angle can be determined that provides information about the dose size.

The optional second detector 22 is disposed in or on the housing 5 at a position suitable for detecting axial movement of the clutch 60. As the clutch 60 is axially entrained when the dosing sleeve 50 moves axially with respect to the housing 5 the second detector 22 may be arranged on the dosing sleeve 50. If the first detector 21 is provided on the dosing sleeve 50, the first and second detectors 21, 22 may be integrated into a single detector unit.

Figure 4:
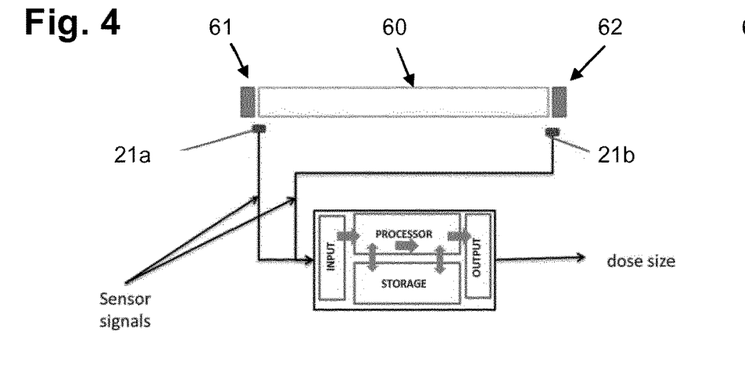
FIG. 4 schematically shows a data processing unit together with sensors.

FIG. 4 shows the first detector 21 with two sensors 21a and 21b located on respective sides of clutch 60 and connected to the data processing unit 20. The processing of the signals from the sensors in the data processing unit 20 is schematically indicated in FIG. 4.

The feature of a data processing unit 20 using the signals of a first detector 21 and, optionally, a second detector 22 for counting the size of the set dose may be applied to other drug delivery devices having a component part, like a sleeve, wheel or ring, performing a certain axial and/or rotational movement only during dose setting and a different movement during dose correcting. Examples for devices into which the data processing unit 20 with the first detector 21 and the second detector 22 may be implemented are disclosed in WO 2014/117944 A1, in WO 2016/016184 A1, in WO 2017/134131 A1 or in WO 2016/001304 A1.

An injection device according to an embodiment of the disclosure may be defined as follows:

An injection device comprising a housing (5) with a receptacle (2) for the product, a dosing mechanism for setting a product dosage to be administered and for displaying the set product dosage, the dosing mechanism comprising a dosing sleeve (50) which is rotatable relative to the housing (5) in a first direction for setting a product dosage and which is rotatable relative to the housing (5) in a second, opposite direction for correcting or dispensing a product dosage, and a dispensing mechanism for dispensing the product, the dispensing mechanism comprising a piston rod (8), which is moveable relative to the housing (5) in a dispensing direction in order to eject the set product dosage in a dispensing stroke corresponding to the set product dosage, at least one sleeve (7; 40), which is rotatable together with the dosing sleeve (50) relative to the housing (5) in the second direction in order to eject the set product dosage, and a clutch (60) interposed between the dosing sleeve (50) and the at least one sleeve (7; 40) and rotatable with the dosing sleeve (50) and/or the at least one sleeve (7; 40), wherein the device further comprises at least a first detector (21) for detecting movement of the clutch (60) relative to the dosing sleeve (50) and/or the housing (5) and/or the at least one sleeve (7; 40) and a data processing unit (20) connected to the first detector (21) for reading, storing, processing, transmitting and/or displaying signals received from the first detector (21). Preferably, the clutch (60) comprises first ratchet teeth (61) for engaging corresponding first teeth (51) of the dosing sleeve (50) such that relative incremental rotation of the dosing sleeve (50) with respect to the clutch (60) in one direction, preferably the first direction, is permitted while prevented in the opposite direction and second ratchet teeth (62) for engaging corresponding second teeth (41) of the at least one sleeve (7; 40) such that relative incremental rotation of the clutch (60) with respect to the at least one sleeve (7; 40) in one direction, preferably the second direction, is permitted while prevented in the opposite direction. In an example, the first detector (21) and/or a further detector are adapted to detect the relative incremental rotation between the clutch (60) and the dosing sleeve (50) and/or the housing (5) and/or the at least one sleeve (7; 40) in the first direction and/or to detect the relative incremental rotation between the clutch (60) and the dosing sleeve (50) and/or the housing (5) and/or the at least one sleeve (7; 40) in the second direction.

For example, in the injection device according to this embodiment the first ratchet teeth (61) and/or the second ratchet teeth (62) are coated with a galvanic conductive material and at least one of the first teeth (51) and/or at least one of the second teeth (41) are provided with an elastic galvanic contact arranged for engaging with the galvanic conductive material at each rotational increment, wherein the first detector (21) comprises the elastic galvanic contact and the galvanic conductive material. According to an alternative example, in the injection device according to this embodiment the first detector (21) comprises at least one mechanical switch which is provided between the first ratchet teeth (61) and the first teeth (51) and/or between the second ratchet teeth (62) and the second teeth (41) and is arranged for detecting engaging of the teeth (51, 61; 41, 62) at each rotational increment.

REFERENCE NUMERALS 1 cap
2 receptacle
2a needle holder
3 cartridge
4 flange
5 housing
6 insert
7 threaded nut
7a toothed ring
7b spring
8 piston rod
8a spline
8b thread
9 threaded sleeve
11a rotary knob
13 spring
14 button
20 data processing unit
21 first detector
21a sensor
21b sensor
22 second detector
30 stop wheel
41 coupling sleeve
41 second teeth
50 dosing sleeve
51 first teeth
60 clutch
61 first ratchet teeth
62 second ratchet teeth

The invention claimed is:

1. An injection device comprising:
a housing with a receptacle for a product;
a dosing mechanism for setting a product dosage to be administered and for displaying the product dosage that has been set, the dosing mechanism comprising:
a dosing sleeve that is rotatable relative to the housing in a first direction for setting the product dosage and that is rotatable relative to the housing in a second direction that is opposite to the first direction for correcting or dispensing the product dosage,
a dispensing mechanism for dispensing the product, the dispensing mechanism comprising a piston rod that is moveable relative to the housing in a dispensing direction in order to eject the product dosage in a dispensing stroke,
at least one sleeve that is rotatable together with the dosing sleeve relative to the housing in the second direction in order to eject the product dosage, and
a clutch interposed between the dosing sleeve and the at least one sleeve and rotatable with the dosing sleeve and/or with the at least one sleeve;
a first detector for detecting movement of the clutch relative to the dosing sleeve and/or to the housing and/or to the at least one sleeve; and
a data processing unit connected to the first detector for reading, storing, processing, transmitting, and/or displaying signals received from the first detector,
wherein the clutch comprises first ratchet teeth for engaging corresponding first teeth of the dosing sleeve such that relative incremental rotation of the dosing sleeve with respect to the clutch in the first direction is permitted while prevented in the second direction and second ratchet teeth for engaging corresponding second teeth of the at least one sleeve such that relative incremental rotation of the clutch with respect to the at least one sleeve in the second direction is permitted while prevented in the first direction.

2. The injection device according to claim 1, wherein the first detector and the data processing unit are adapted to detect at least one of a rotational movement of the clutch, an angle of rotation of the rotational movement of the clutch, and a direction of the rotational movement of the clutch.

3. The injection device according to claim 1, wherein the data processing unit is adapted to provide information about a dose size and/or an amount of product ejected from the injection device by the dispensing mechanism and/or the maximum dose set by the dosing mechanism based on a rotation protocol containing data received from the first detector.

4. The injection device according to claim 1, wherein the first detector and/or an additional detector are adapted to detect the relative incremental rotation between the clutch and the dosing sleeve and/or the housing and/or the at least one sleeve in the first direction and/or in the second direction.

5. The injection device according to claim 1, wherein the relative incremental rotation between the clutch and the dosing sleeve and/or the at least one sleeve.

6. The injection device according to claim 1, wherein the first ratchet teeth and/or the second ratchet teeth are coated with a galvanic conductive material.

7. The injection device according to claim 1, wherein the first detector comprises at least one mechanical switch that is provided between the first ratchet teeth and the first teeth and/or between the second ratchet teeth and the second teeth and is arranged for detecting engagement of the first ratchet teeth, the first teeth, the second ratchet teeth, and/or the second teeth at each rotational increment.

8. The injection device according to claim 1, wherein the first detector comprises at least one of a magnetic sensor and an inductive sensor.

9. The injection device according to claim 1, further comprising a second detector for detecting the relative axial position of the clutch and the dosing sleeve.

10. The injection device according to claim 9, wherein the second detector comprises at least one of a magnetic sensor and an inductive sensor.

11. The injection device according to claim 8, wherein the clutch and/or the dosing sleeve comprise a metallic material.

12. The injection device according to claim 9, wherein the data processing unit is adapted to provide information about the infection device being in a dose setting mode, a dose correction mode, or a dose dispensing mode based on data received from the first detector and the second detector.

13. The injection device according to claim 1, wherein the data processing unit is a separate component part provided detachable from the housing.

14. The injection device according to claim 1, further comprising a cartridge containing the product.

15. The injection device according to claim 5, wherein the first ratchet teeth and the second ratchet teeth are located on the clutch facing in opposite axial directions.

16. The injection device according to claim 9, wherein the data processing unit is connected to the second detector for reading, storing, processing, transmitting, and/or displaying signals received from the second detector.

17. The injection device according to claim 1, wherein the data processing unit is located in or on the housing.

18. The injection device according to claim 6, wherein at least one of the first teeth and/or at least one of the second teeth are provided with an elastic galvanic contact arranged for engaging with the galvanic conductive material at each rotational increment.

19. The injection device according to claim 18, wherein the first detector comprises the elastic galvanic contact and the galvanic conductive material.

\* \* \* \* \*

UNITED STATES PATENT AND TRADEMARK OFFICE
CERTIFICATE OF CORRECTION

| | | |
|---|---|---|
| PATENT NO. | : 11,724,039 B2 | |
| APPLICATION NO. | : 16/976202 | |
| DATED | : August 15, 2023 | |
| INVENTOR(S) | : Stefan Blancke | |

It is certified that error appears in the above-identified patent and that said Letters Patent is hereby corrected as shown below:

In the Claims

In Column 14, Line 57, Claim 5, after "sleeve" insert -- generates an acoustic feedback --

Signed and Sealed this
Thirteenth Day of February, 2024

Katherine Kelly Vidal
*Director of the United States Patent and Trademark Office*